United States Patent [19]
Rcraw et al.

[11] Patent Number: 6,020,692
[45] Date of Patent: Feb. 1, 2000

[54] MARCO LAMP LIFE EXTENSION IN INSTALLATION FOR ADI, AEI

[75] Inventors: Danniel Rcraw, Churan; Tsun-Ching Lin; Ren-Zhi Demg, both of Chu-Tong; Chin-Chuan Kuo, Hsin-Chu, all of Taiwan

[73] Assignee: Taiwan Semiconductor Manufacturing Company, Ltd, Hsin-Chu, Taiwan

[21] Appl. No.: 09/283,065

[22] Filed: Mar. 31, 1999

[51] Int. Cl.⁷ ..................................................... H05B 37/00
[52] U.S. Cl. .......................... 315/320; 315/322; 315/295; 307/137; 307/157; 356/237
[58] Field of Search .................................... 315/320, 322, 315/313, 362, 208, 295; 307/137, 157, 139, 141.4, 141.8; 356/237, 239; 362/14

[56] References Cited

U.S. PATENT DOCUMENTS

| | | | |
|---|---|---|---|
| 4,001,777 | 1/1977 | Alexander | 340/434 |
| 5,753,983 | 5/1998 | Dickie et al. | 307/141.4 |
| 5,917,588 | 6/1999 | Addiego | 356/237 |

*Primary Examiner*—Haissa Philogene
*Attorney, Agent, or Firm*—Tung & Associates

[57] ABSTRACT

A circuit for use with optical inspection lamps, e.g., tungsten-halogen or Marco lamps, in semiconductor fabrication machines performing ADI and AEI operations, that will lower the operating voltage of the lamps when the machine is not being used by an operator, while providing full light intensity during optical inspections. The circuit is coupled into the Marco lamp power supply and contains two micro-switches, each containing two sets of switch contacts normally configured with one set closed and one set open to render one micro-switch closed providing the operating voltage to the lamp and the other open rendering the circuit inactive in this condition. The micro-switches have operating levers that cooperate with indexes which follow the position of cassette elevators that deliver the semiconductor wafers for processing and each of which has an "up" and a "down" position. When the two indexes are "up", the machine is not in use, and each micro-switch will have its lever engaged closing their normally open contact sets which closes both micro-switches and introduces a resistor, coupled to the normally opened micro-switch, into the circuit causing its activation. Activation with the added resistance causes the lamp loading voltage to lower and the light intensity to decrease, extending the life of the lamp by decreasing its power during periods when it is not needed, while allowing the lamp to be left ON.

18 Claims, 2 Drawing Sheets

MARCO LAMP LIFE EXTENSION IN INSTALLATION FOR ADI, AEI

FIELD OF THE INVENTION

The present invention relates generally to optical inspection lamps and, more particularly, to a method and means for extending the life of optical inspection lamps, such as tungsten-halogen lamps or Marco lamps, that are used for inspecting in processing machine installations, e.g., with semiconductor fabrication equipment, for after develop inspection (ADI) or after etch inspection (AEI).

BACKGROUND OF THE INVENTION

In inspection systems used with processing machine installations, such as for semiconductor fabrication ADI and AEI operations, the lamps that are used for illumination during optical inspections are of the tungsten-halogen type, and particularly are called Marco lamps, which typically are operated 24 hours a day irrespective of whether they are needed by the machine operators. This continuous operation is due to the fact that such lamps have a start-up phase that causes the tungsten to vaporize and combine with the halogen atoms but, as the bulb walls may still be too cold to allow the cycle to start, the vaporized material returns to the filament and start-up becomes difficult and power consuming. Consequently, once the lamp is successfully started there is a reluctance on the part of the machine operators to turn it off when not needed and then later to attempt the start up process again when use is required.

Tungsten-halogen lamp characteristics are known and it is clear, as seen in FIG. 1, that if the operating voltage is 10–12% lower than the specified voltage, the lamp life time will be lengthened. The particular tungsten-halogen lamp, the Marco lamp, that is used in ADI and AEI operations is a constant current device and is independent of the operation of the fabrication machines. If, in order to reduce the specified operating voltage and extend the lamp life, a voltage-dropping resistance is included in the lamp circuit, the intensity of the light produced will be lowered, resulting in dissatisfaction on the part of the machine operators since it will become more difficult to identify defects such as photoresist pitting or particle contamination. At present no system exists for achieving an adequate balance between long lamp life and optimum lamp intensity and operation.

It is therefore an object of the present invention to provide a longer life for tungsten-halogen lamps in inspection machines without reducing the operating light intensity of the lamp and degrading the inspection operation.

It is another object of the invention to provide a longer life Marco lamp for use in ADI and AEI operations without reducing the lamp intensity or operating effectiveness during inspections.

SUMMARY OF THE INVENTION

In accordance with the present invention, a circuit is provided for use with optical inspection systems, particularly with lighting devices such as tungsten-halogen lamps, and, in a preferred embodiment, Marco lamps in semiconductor fabrication machines performing ADI and AEI operations, which circuit will lower the operating voltage of the lamps when the machine is not being used by an operator while providing fill light intensity during optical inspections. The circuit is coupled into a Marco lamp power supply and contains two micro-switches, each containing two sets of switch contacts configured to render one micro-switch normally open and the other normally closed. The micro-switches have operating levers that cooperate with ADI, or AEI, indexes which follow the position of the cassette elevators that deliver the semiconductor wafers for processing. There are two indexes, each having an "up" and a "down" position. An index in the "up" position engages the operating lever of its respective micro-switch and causes an alternate switch contact set to close. When an index is in the "up" position the elevator will be in a position that indicates the operator may not be using the machine. Accordingly, when the two indexes are "up", the indication is clear that the machine is not in use, and the open micro-switch will have its lever engaged and alternate contact set closed. Closing of both alternate contact sets closes both micro-switches and introduces a voltage-dropping element, e.g., a resistor, coupled to the normally opened micro-switch, into the circuit causing its activation. Activation of the circuit with the added resistance causes the Marco lamp loading voltage to lower and the intensity to decrease, resulting in the extension of the life of the lamp by decreasing its power during periods when it is not needed, while allowing the lamp to be left ON. The decreased power ON condition enables the lamp to be ready for the next start-up to full power and illumination when the circuit is deactivated by movement of the indexes to the "down" position indicating machine operation.

BRIEF DESCRIPTION OF THE DRAWINGS

These and other objects, features and advantages of the present invention will become apparent from the following detailed description and the appended drawings in which.

DETAILED DESCRIPTION OF THE PREFERRED EMBODIMENT

The present invention is directed to a method and means for extending the life of optical inspection lamps such as tungsten-halogen lamps used in processing machinery, and in a preferred embodiment Marco lamps that are used in inspection machine installations in semiconductor fabrication equipment for after develop inspection (ADI) or after etch inspection (AEI). The invention involves a circuit that cooperates with the ADI, or AEI, indexes which follow the positions of the cassette elevators that deliver the semiconductor wafers for processing. The circuit includes two micro-switches, each containing two sets of switch contacts configured to render one micro-switch normally open and the other normally closed. The micro-switches cooperate with ADI, or AEI, indexes such that when the two indexes are "up", indicating that the elevators are in a position wherein the operator is not using the machine, the open micro-switch will be touched and an alternate set of switch contacts closed causing the circuit to be activated with the introduction of a resistance. Activation of the circuit with the added resistance causes the Marco lamp loading voltage to lower, preferably about 10–12%, resulting in the extension of the life of the lamp by decreasing its power and intensity during periods when it is not needed while still allowing the lamp to be left ON ready for start-up.

Figure 1:
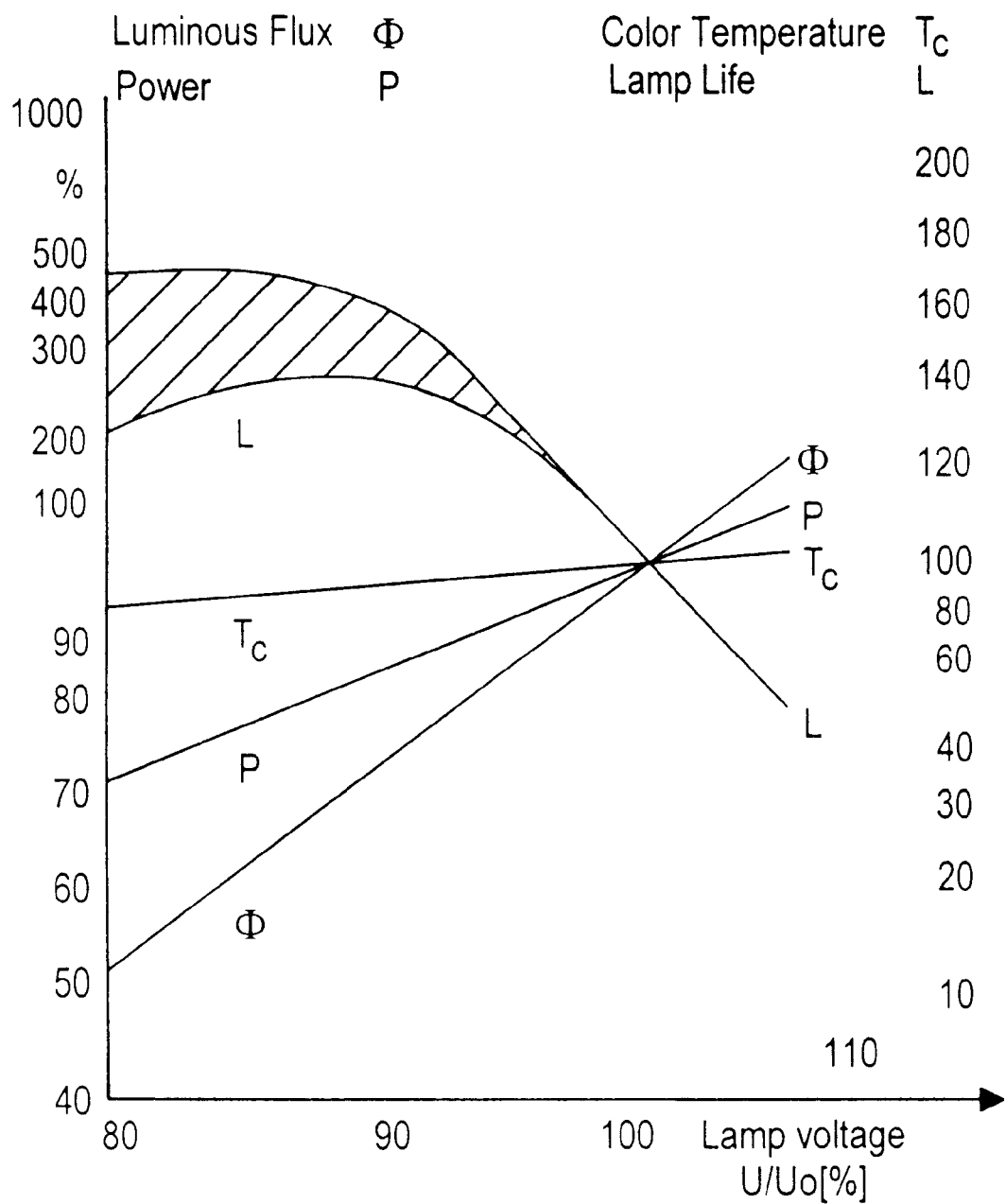
FIG. 1 is an illustration of known tungsten-halogen lamp characteristics showing that if the operating voltage is 10–12% lower than the specified voltage, the lamp life time will be lengthened.
Figure 2:
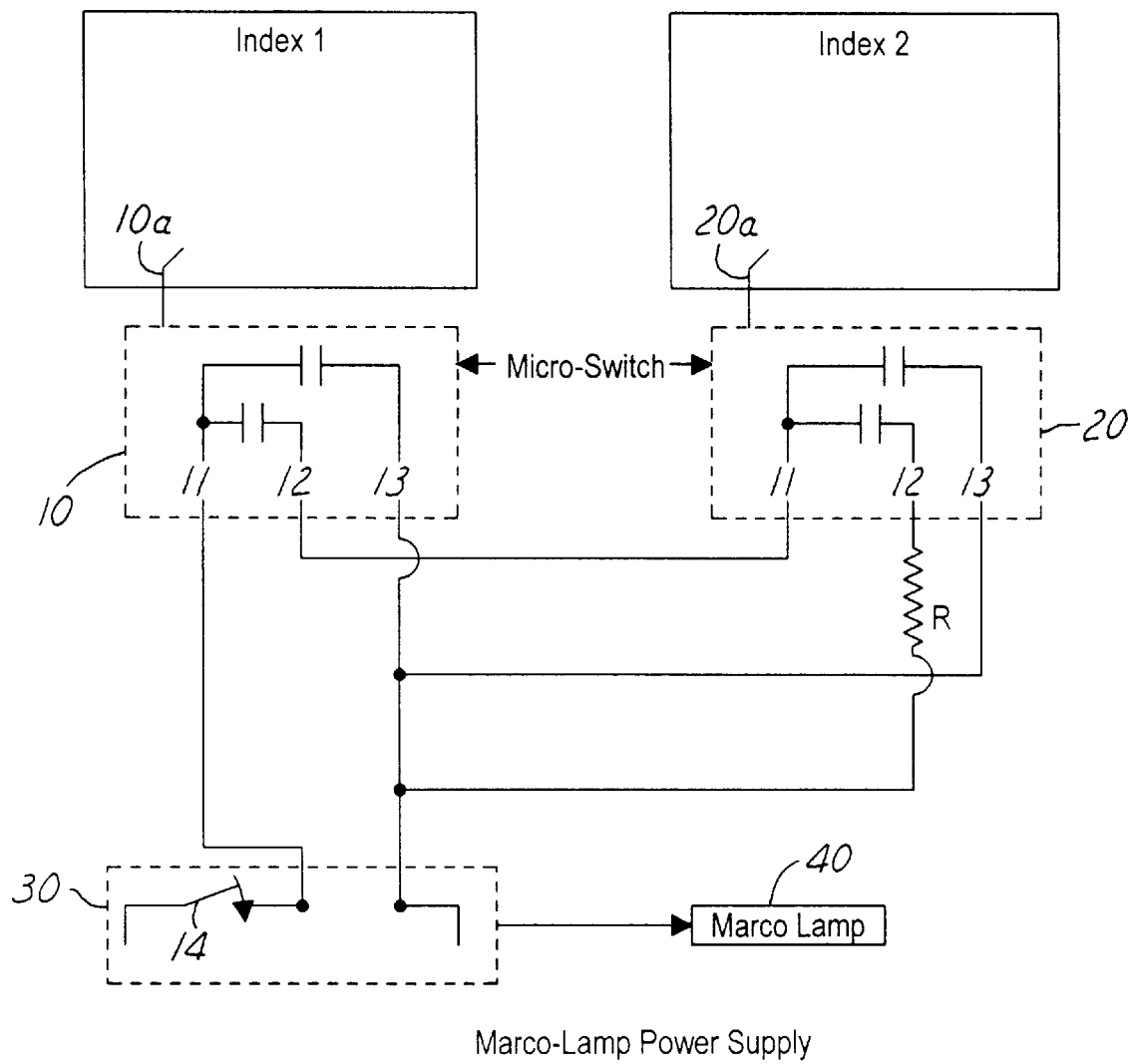
FIG. 2 illustrates a circuit in accordance with the present invention for controlling the power supply to a Marco lamp disposed in a semiconductor fabricating machine and showing the relationship between the cassette elevator ADI or AEI index and the micro-switches activating the circuit.

More particularly, a preferred embodiment of a circuit in accordance with the invention is shown in FIG. 2 and includes respective micro-switches 10 and 20 with operating levers 10a and 20a disposed adjacent Index 1 and Index 2 of ADI or AEI carrier holders in a semiconductor fabrication machine. Each micro-switch 10 and 20 contains two sets of contacts or switches, 11 and 12, and 11 and 13. Switch contacts 11–13 are normally closed and switch contacts 11–12 are normally open. Switch contact 11 of micro-switch 10 is connected to one side of a manual switch 14, normally closed, for coupling a power supply 30 to a Marco lamp 40. The other side of switch 14 is coupled to switch contacts 13 of micro-switches 10 and 20, as well as to contact 12 of micro-switch 20 through a resistor R. Contact 12 of micro-switch 10 is coupled to contact 11 of micro-switch 20. Engagement of the operating levers 10a and 20a with their Indexes 1 and 2 will close their respective switch contacts 11–12. Thus, when an index in the "up" position engages the operating lever of its respective micro-switch an alternate switch contact set is closed.

With this switch contact arrangement or configuration, and with both of the Indexes 1 and 2 in the "down" position indicating the machine is in use, lamp 40 is powered through a path including closed lamp switch 14 and closed switch contacts 11–13 in micro-switch 10. As switch contacts 11–12 in micro-switch 10 are normally open, micro-switch 20 will be open since its contact 11 is coupled to open switch contacts 11–12 of micro-switch 10, and thus no current path will be closed through either normally closed switch contacts 11–13 or open contacts 11–12 in micro-switch 20 across switch 14. When either of the operating levers, 10a and 20a, is engaged with its Index, 1 and 2, its respective switch contacts 11–12 will be closed and its switch contacts 11–13 will open. When both operating levers are engaged, a path will be completed across switch 14 through the respective contacts 11–12 and resistor R.

It then will be seen that in operation, when Index 1 is "down", as shown, the lever 10a of micro-switch 10 is untouched, so that the circuit completed across switch 14 through contacts 11–13 is unchanged, and the switch 11–12 remains open. But, when Index 1 is moved to the "up" position, micro-switch lever 10a is touched or engaged causing its switch contacts 11–12 to be closed, which completes a circuit across switch 14 through switch 11–13 of micro-switch 20. In both instances, there is little or no change in the power to the lamp 40. When Index 2 is "down", lever 20a of micro-switch 20 is untouched, leaving the circuit through its closed contacts 11–13 unchanged, while, when Index 2 is moved to the "up" position, micro-switch lever 20a is engaged opening contacts 11–13 and closing its contacts 11–12. In the latter case, if the contacts 11–12 of micro-switch 10 are still open, indicating Index 1 is "down", then no closed path is formed across switch 14 through closed contacts 11–12 of micro-switch 20. However, when both Indexes 1 and 2 are "up", indicating the machine is not being used, the contacts 11–12 in both micro-switches 10 and 20 will be closed connecting the resistor R across switch 14. This condition causes a drop in the operating voltage from the power supply 30 to the lamp 40.

It will accordingly be appreciated that the activation of the circuit with the addition of resistance R when the machine is not in use causes the Marco lamp loading voltage to lower and the light intensity to decrease, resulting in the extension of the life of the lamp by decreasing its power during periods when it is not needed, while allowing the lamp to be left ON. The decreased power ON condition enables the lamp to be ready for the next start-up to full power and illumination when the circuit is deactivated by movement of the indexes to the "down" position indicating machine operation.

In a specific working example, the capacitance across the respective switch contacts may be of the order of 0.1 microfarads and the resistance R may have a value of 50 K ohms. These values should produce a lamp operating voltage that is 10–12% lower than the specified voltage.

While the present invention has been described in an illustrative manner, it should be understood that the terminology used is intended to be in a nature of words of description rather than of limitation. Furthermore, although the invention has been described in terms of a preferred embodiment, it is to be appreciated that those of skill in the art will readily apply these teachings to other possible variations of the invention.

The embodiment of the invention in which an exclusive property or privilege is claimed are defined in the following claims:

What is claimed is:

1. A circuit for extending the life of a lamp used for inspecting in processing machinery that has at least two operating elements each including an index with first and second conditions respectively indicating whether the machinery is being operated or not in use, comprising:

means, having a first connection and a second connection, for coupling said lamp to a specified voltage from a power supply;

at least two micro-switches, each connected across said first and second connections and each containing two sets of switch contacts, said switch contacts being normally configured with one set in each micro-switch open and the other set closed;

means on each of said micro-switches for cooperating with a respective operating element index such that when an index is in said first condition the respective sets of switch contacts are in the normal configuration and when an index is in said second condition said sets of switch contacts are switched to an alternate configuration; and voltage dropping means, coupled across said first and second connections when both of said indexes are in said second condition and said switch contacts are in said alternate configuration, for decreasing the magnitude of said specified voltage while maintaining the operation of said lamp.

2. A circuit as in claim 1 wherein said lamp is a tungsten-halogen lamp.

3. A circuit as in claim 2 wherein said tungsten-halogen lamp is a Marco lamp.

4. A circuit as in claim 1 wherein said voltage dropping means comprises a resistor.

5. A circuit as in claim 1 wherein the normally closed switch contacts in one of said micro-switches are connected directly across said first and second connections, and the normally closed switch contacts in the other micro-switch are connected across said first and second connection through the normally open switch contacts in the other micro-switch.

6. A circuit as in claim 1 wherein said voltage dropping means is connected across said first and second connections in series with the normally open switch contacts in said micro-switches.

7. A circuit as in claim 1 wherein said voltage dropping means comprises means for dropping the voltage from said power supply 10–12% lower than the specified voltage.

8. A circuit as in claim 1 wherein said operating elements are elevators and said first and second conditions are the "down" and "up" positions of said elevators.

9. A circuit as in claim 1 wherein said means on each of said micro-switches for cooperating with a respective operating element index comprises a switch contact operating lever engageable by said respective operating element index.

10. A method for extending the life of a lamp used for inspecting in processing machinery that has at least two operating elements each including an index with first and second conditions respectively indicating whether the machinery is being operated or not in use, comprising the steps of:

providing a first connection and a second connection for coupling said lamp to a specified voltage from a power supply;

connecting at least two micro-switches across said first and second connections and providing in each micro-switch two sets of switch contacts, said switch contacts being normally configured with one set in each micro-switch open and the other set closed;

disposing each of said micro-switches for cooperating with a respective operating element index such that when an index is in said first condition the respective sets of switch contacts are in the normal configuration and when an index is in said second condition said sets of switch contacts are switched to an alternate configuration; and coupling a voltage dropping element across said first and second connections when both of said indexes are in said second condition and said switch contacts are in said alternate configuration, for decreasing the magnitude of said specified voltage while maintaining the operation of said lamp.

11. A method as in claim 10 wherein said lamp is a tungsten-halogen lamp.

12. A method as in claim 11 wherein said tungsten-halogen lamp is a Marco lamp.

13. A method as in claim 10 wherein said voltage dropping element comprises a resistor.

14. A method as in claim 10 wherein the normally closed switch contacts in one of said micro-switches are connected directly across said first and second connections, and the normally closed switch contacts in the other micro-switch are connected across said first and second connection through the normally open switch contacts in the other micro-switch.

15. A method as in claim 10 wherein said voltage dropping element is connected across said first and second connections in series with the normally open switch contacts in said micro-switches.

16. A method as in claim 10 wherein said voltage dropping element is selected to drop the voltage from said power supply 10–12% lower than the specified voltage.

17. A method as in claim 10 wherein said operating elements are elevators and said first and second conditions are the "down" and "up" positions of said elevators.

18. A method as in claim 10 wherein each of said micro-switches cooperate with a respective operating element index by means of a switch contact operating lever engageable by said respective operating element index.

* * * * *